(12) United States Patent
Fukai et al.

(10) Patent No.: US 9,995,779 B2
(45) Date of Patent: Jun. 12, 2018

(54) SENSING DEVICE AND SENSING METHOD

(71) Applicant: TERUMO KABUSHIKI KAISHA, Tokyo (JP)

(72) Inventors: Toshio Fukai, Kanagawa (JP); Atsushi Matsumoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 14 days.

(21) Appl. No.: 14/698,607

(22) Filed: Apr. 28, 2015

(65) Prior Publication Data

US 2015/0247887 A1    Sep. 3, 2015

Related U.S. Application Data

(63) Continuation of application No. PCT/JP2012/078298, filed on Nov. 1, 2012.

(51) Int. Cl.
| | |
|---|---|
| *G01N 33/48* | (2006.01) |
| *G01R 29/26* | (2006.01) |
| *A61B 5/145* | (2006.01) |
| *A61B 5/00* | (2006.01) |
| *G01N 33/66* | (2006.01) |
| *G06G 7/58* | (2006.01) |

(52) U.S. Cl.
CPC .......... *G01R 29/26* (2013.01); *A61B 5/14532* (2013.01); *A61B 5/725* (2013.01); *G01N 33/66* (2013.01)

(58) Field of Classification Search
CPC .............................. G01N 33/66; G01N 33/582
See application file for complete search history.

(56) References Cited

U.S. PATENT DOCUMENTS

| | | |
|---|---|---|
| 2005/0027182 A1 | 2/2005 | Siddiqui et al. |
| 2005/0272985 A1 | 12/2005 | Kotulla et al. |
| 2007/0060803 A1 | 3/2007 | Liljeryd et al. |

FOREIGN PATENT DOCUMENTS

| | | |
|---|---|---|
| JP | 2005-131370 | 5/2005 |
| JP | 2007-516783 | 6/2007 |
| JP | 2007-523709 | 8/2007 |
| WO | WO 2005/082233 | 9/2005 |

OTHER PUBLICATIONS

International Search Report (with English translation) for International Patent Application No. PCT/JP2012/078298, dated Jan. 8, 2013, 6 pages.
Written Opinion (English translation) for International Patent Application No. PCT/JP2012/078298, dated Jan. 8, 2013, 6 pages.

*Primary Examiner* — Eric S Dejong
(74) *Attorney, Agent, or Firm* — Sheridan Ross P.C.

(57) ABSTRACT

The present invention relates to a sensing device and a sensing method for continuously or intermittently quantifying a concentration of analyte. A measurement signal correlated with a concentration of analyte is sequentially acquired by use of a sensor (12). A filter processing is performed on a time sequence of the measurement signal acquired by the sensor (12) in a frequency domain via one type of filter among a plurality of types of filters (48, 49, 84). One type of filter used in the filter processing is switched depending on the amount of temporal change of the measurement signal.

20 Claims, 12 Drawing Sheets

| h0 | h1 | h2 | h3 | h4 |
|---|---|---|---|---|
| 0.159 | 0.220 | 0.243 | 0.220 | 0.159 |

| h0 | h1 | h2 | h3 | h4 |
|---|---|---|---|---|
| 0.301 | 0.398 | 0.301 | 0.000 | 0.000 |

SENSING DEVICE AND SENSING METHOD

CROSS-REFERENCE TO RELATED APPLICATIONS

This application is a continuation of and claims priority to PCT/JP2012/078298, filed Nov. 1, 2012, entitled "Sensing Device and Sensing Method", which is incorporated herein by reference in its entirety and for all purposes.

TECHNICAL FIELD

The present invention relates to a sensing device and a sensing method for continuously or intermittently quantifying a concentration of analyte.

BACKGROUND ART

For example, there is recently developed a continuous glucose monitoring system (also referred to as CGM system) for continuously or intermittently quantifying a concentration of glucose in blood as analyte with a sensor unit embedded in the body of a subject to be tested. When a measurement signal is acquired via the sensor unit, various noises including electric noises or light quantity noises are typically mixed into the measurement signal. Thus, there are proposed various filtering techniques for effectively removing noise components in order to enhance an accuracy of quantifying a concentration of glucose.

JP 2005-131370 A proposes therein a method for removing noise components by use of a filtering algorithm (particularly Kalman filter) in a time domain. More specifically, it describes therein that an error covariance matrix is defined by a function of signal difference parameter (such as standard deviation) so that a filter coefficient is dynamically optimized.

SUMMARY OF INVENTION

Technical Problem

It is desired in terms of design that the amount of processing calculations by an electric circuit is reduced to the minimum in order to downsize a device and to reduce consumed power. However, there is a problem that the amount of processing calculations tends to increase with the method described in JP 2005-131370 A and the above desire is not to be addressed.

The present invention has been made in order to solve the problem, and it is an object thereof to provide a sensing device and a sensing method for keeping a following capability for a temporal change in concentration of analyte while effectively removing noise components from a measurement signal by use of a filter in a frequency domain in a relatively simple structure.

Solution to Problem

A sensing device according to the present invention is directed for continuously or intermittently quantifying a concentration of analyte, and includes a sensor unit for sequentially acquiring a measurement signal correlated with the concentration of analyte, a filtering unit including a plurality of types of filters for performing a filter processing on a time sequence of the measurement signal acquired by the sensor unit in a frequency domain via one type of filter among the plurality of types of filters, and a filter processing unit for switching the one type of filter used in the filter processing depending on the amount of temporal change of the measurement signal.

In this way, the filter processing unit for changing one type of filter used in a filter processing in a frequency domain depending on the amount of temporal change of a measurement signal is provided thereby to select a filter as needed in consideration of phase delay property due to a temporal change of the measurement signal and the filter processing. Thereby, a noise component can be effectively removed from the measurement signal by use of a filter in a frequency domain with a relatively simple structure while a following capability for a temporal change in concentration of analyte can be kept.

The filtering unit includes at least an identity transformation filter for performing identity transformation on a time sequence of the measurement signal, and the filter processing unit preferably switches to the identity transformation filter when the amount of temporal change is larger than a threshold. Phase delay due to a filter processing is not caused when the amount of temporal change is larger than a threshold, and thus the following capability for a temporal change in concentration of analyte can be kept.

Further, the filtering unit includes at least two types of filters with different average values of the amount of phase delay in a band at a cutoff frequency or less, and the filter processing unit preferably switches to the filter with a low average value of the amount of phase delay when the amount of temporal change is large, and switches to the filter with a high average value of the amount of phase delay when the amount of temporal change is small. Phase delay due to a filter processing is not caused when the amount of temporal change is large, and thus the following capability for a temporal change in concentration of analyte can be kept. When the amount of temporal change is small, the following capability is less required, and thus a noise component can be more effectively removed from the measurement signal.

A sensing method according to the present invention is directed for continuously or intermittently quantifying a concentration of analyte, and includes an acquiring step of sequentially acquiring a measurement signal correlated with the concentration of analyte, a processing step of performing a filter processing on a time sequence of the measurement signal acquired by the sensor in a frequency domain via one type of filter among a plurality of types of filters, and a switching step of switching the one type of filter used in the filter processing depending on the amount of temporal change of the measurement signal.

The plurality of types of filters includes at least an identity transformation filter for performing identity transformation on a time sequence of the measurement signal, and switching is preferably made to the identity transformation filter when the amount of temporal change is larger than a threshold in the switching step.

Further, the plurality of types of filters includes at least two types of filters with different average values of the amount of phase delay in a band at a cutoff frequency or less, and switching is preferably made to the filter with a low average value of the amount of phase delay when the amount of temporal change is large, and to the filter with a high average value of the amount of phase delay when the amount of temporal change is small in the switching step.

Advantageous Effects of Invention

With the sensing device and the sensing method according to the present invention, one type of filter used in a filter processing in a frequency domain is switched depending on the amount of temporal change of a measurement signal, and thus a filter can be selected as needed in consideration of phase delay property due to a temporal change in the measurement signal and the filter processing. Thereby, a noise component can be effectively removed from a measurement signal by use of a filter in a frequency domain in a relatively simple structure while the following capability for a temporal change in concentration of analyte can be kept.

DESCRIPTION OF EMBODIMENTS

A sensing method according to the present invention will be described below with reference to the accompanying drawings by use of preferred embodiments for a relationship with a sensing device.

[Structure of Sensing Device 10 Common in First and Second Embodiments]

A structure of a sensing device 10 common in first and second embodiments will be first described with reference to the schematic block diagram of FIG. 1.

Figure 1:
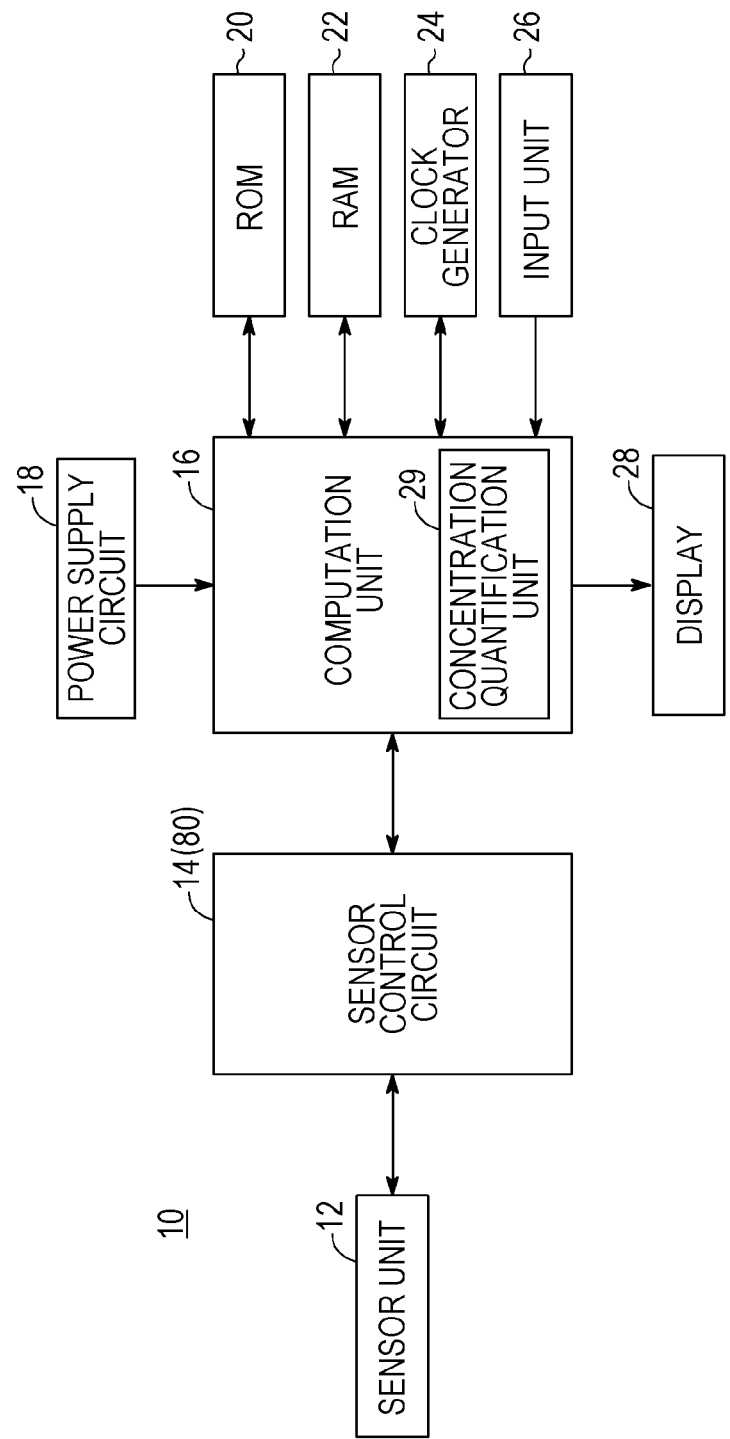
FIG. 1 is a schematic block diagram of a sensing device common in first and second embodiments.

As illustrated in FIG. 1, the sensing device 10 basically includes a sensor unit (sensor) 12, a sensor control circuit 14 (sensor control circuit 80), a calculation unit 16, a power supply circuit 18, a ROM (Read Only Memory) 20, a RAM (Random Access Memory) 22, a clock generator 24, an input unit 26, and a display 28.

The sensor unit 12 acquires a signal correlated with a concentration of analyte (denoted as measurement signal S below). The sensor unit 12 preferably employs an optical sensor (such as fluorescent sensor) capable of easily changing a sampling interval Ts. A form of the sensor unit 12 is not limited thereto, and may employ a sensor for electrically (electrochemically) measuring a glucose level with an enzymatic electrode method using enzyme such as glucose oxidase (GOD), for example.

The sensor control circuit 14 controls to drive the sensor unit 12 thereby to acquire a measurement signal S at a desired timing. The sensor control circuit 14 converts a current value (analog signal) as the measurement signal S into a voltage value, and quantizes the voltage value and converts it into a digital signal. The sensor control circuit 14 performs a predetermined filter processing on the analog signal or digital signal, thereby removing noise components mixed into the measurement signal S.

The calculation unit 16 is configured of CPU (Central Processing Unit), MPU (Micro-Processing Unit), or the like, and reads programs previously stored in the ROM 20 thereby to perform various signal processings described below. The calculation unit 16 functions as a concentration quantification unit 29 for quantifying a concentration of analyte based on a signal value Sf(k) acquired from the sensor control circuit 14.

The power supply circuit 18 supplies power to each component in the sensing device 10 including the calculation unit 16. The RAM 22 can read or write various items of data required for performing the sensing method according to the present invention in addition to a measurement signal S input via the sensor unit 12. The clock generator 24 generates a clock signal at a predetermined cycle, and supplies it to the calculation unit 16. Thereby, the calculation unit 16 can control a timing to acquire a signal value Sf(k).

The input unit 26 is provided to input various items of information (such as quantification interval Td) provided for calculations in the calculation unit 16. For example, it may be a press button, or a touch panel incorporated in the display 28. The display 28 visualizes and displays various items of information on a concentration of analyte quantified by the calculation unit 16 (also referred to as quantification concentration below). The display 28 is a display module capable of monochrome or color display, and may be configured of a liquid crystal panel, organic EL (Electro-Luminescence), inorganic EL panel, or the like.

The sensor unit 12 is applicable to a variety of usage such as enzyme sensor, glucose sensor, pH sensor, immunity sensor, and microbe sensor. For example, a structure of the sensor unit 12 may employ various structures, not limited to the structure. For example, the sensor control circuit 14 (80) and the calculation unit 16, which are physically separated, are wirelessly communicable with each other so that the sensor unit 12 can intermittently or continuously quantify while being completely embedded in the body of a subject to be tested. Wireless communication may employ a short-distance communication standard (such as body area network defined in "IEEE 802.15.6").

First Embodiment

Subsequently, a structure and operations of the sensor control circuit 14 according to the first embodiment will be described with reference to FIGS. 2 to 7. A quantification operation using glucose as analyte will be mainly described in the present specification.

[Block Diagram of Sensor Control Dircuit 14]

Figure 2:
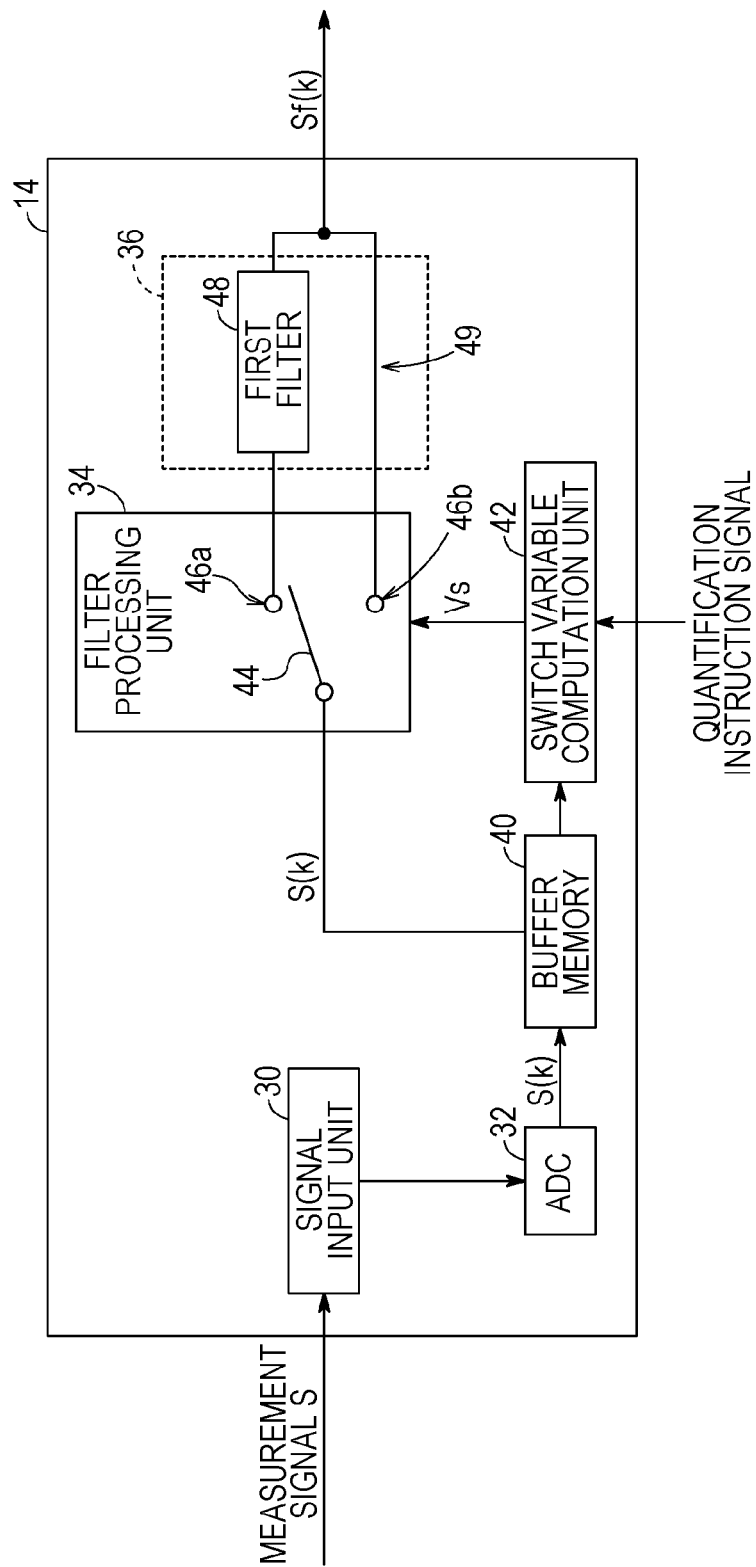
FIG. 2 is a block diagram of a sensor control circuit according to the first embodiment.

FIG. 2 is a block diagram of the sensor control circuit 14 (see FIG. 1) according to the first embodiment.

The sensor control circuit 14 includes a signal input unit 30 for inputting a measurement signal S from the sensor unit 12, an A/D converter (denoted as ADC 32 below) for converting a measurement signal S as an analog signal into an original signal value S(k) as a digital signal, a filter processing unit 34 for selectively switching one type of filter among a plurality of types of filters, a filtering unit 36 for performing a filter processing on an original signal value S(k) in a frequency domain, a buffer memory 40 for temporarily storing a latest original signal value S(k), and a switch variable computation unit 42 for computing a variable for switching a plurality of types of filters (denoted as switch variable Vs) provided in the filter processing unit 34.

A switch 44 in the filter processing unit 34 may be in a state (ON state) in which it is connected to either a first terminal 46a or a second terminal 46b or in a state (OFF state) in which it is connected to neither the first terminal 46a nor the second terminal 46b.

The filtering unit 36 includes a first filter 48 for performing a filtering processing in a frequency domain. The first filter 48 is connected to the first terminal 46a in the filter processing unit 34. On the other hand, no filter is connected to the second terminal 46b in the filter processing unit 34. In other words, the filtering unit 36 further includes an identity transformation filter 49 for performing identity transformation on an original signal value S(k).

Figure 3:
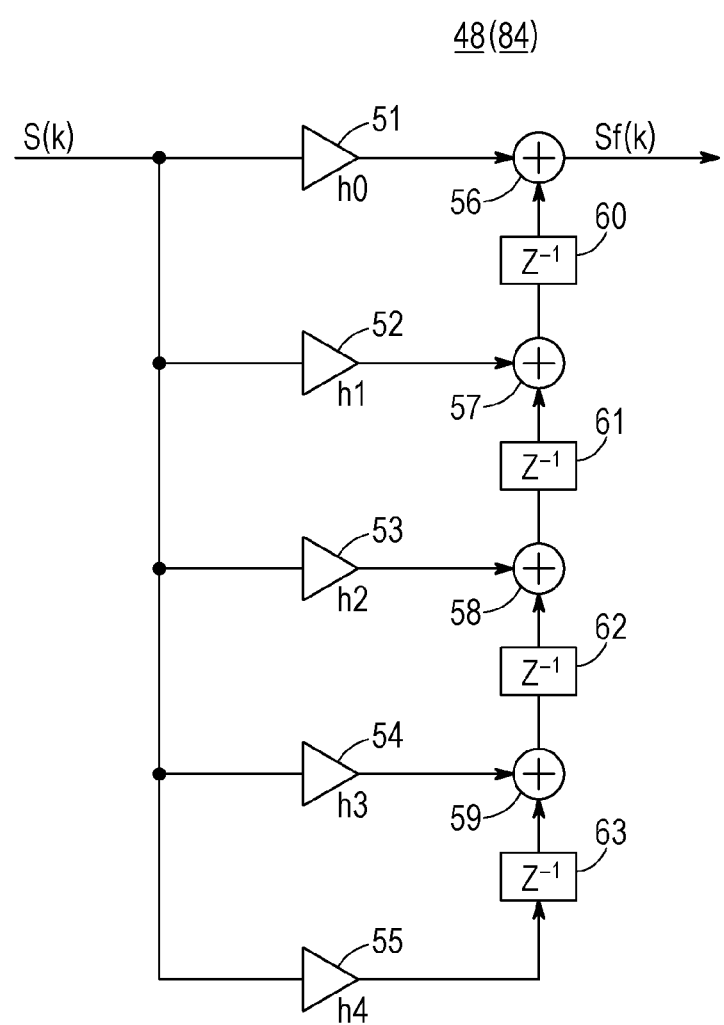
FIG. 3 is a circuit configuration diagram of a first filter illustrated in FIG. 2

FIG. 3 is a circuit configuration diagram of the first filter 48. The first filter 48 is configured of five multipliers 51, 52, 53, 54, 55, four adders 56, 57, 58, 59, and four delay devices 60, 61, 62, 63. That is, the first filter 48 corresponds to a FIR (Finite Impulse Response) filter having five taps. Multiplier factors (denoted as filter coefficients below) set for the multipliers 51 to 55 are denoted as h0, h1, h2, h3, and h4 in this order, respectively. The FIR filter is a well-known electric circuit, and thus an explanation of the function and connection relationship of each computation device will be omitted.

Figures 4A, 4B:
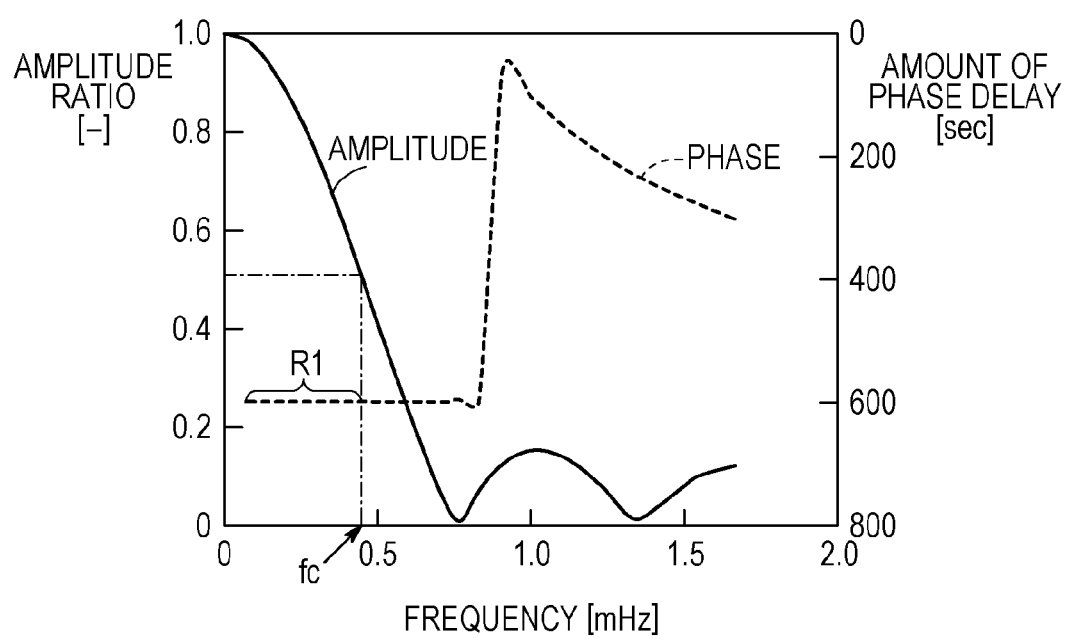
FIG. 4A is a diagram of filter coefficients of the first filter illustrated in FIG. 2
FIG. 4B is a graph illustrating a filter property depending on the filter coefficients of FIG. 4A.

FIG. 4A is a diagram illustrating the filter coefficients of the first filter 48 illustrated in FIG. 2. Specifically, a filter coefficient of the multiplier 51 (see FIG. 3 below), a filter coefficient of the multiplier 52, a filter coefficient of the multiplier 53, a filter coefficient of the multiplier 54, and a filter coefficient of the multiplier 55 are set at h0=0.159, h1=0.220, h2=0.243, h3=0.220, and h4=0.159, respectively.

FIG. 4B is a graph illustrating a filter property depending on the filter coefficients of FIG. 4A.

The horizontal axis in a solid line in the graph indicates frequency (unit: mHz) and the vertical axis indicates amplitude ratio (unit: no). The amplitude ratio is a ratio of an amplitude of an output signal relative to an amplitude of an input cyclic signal (sinusoidal waveform signal). Ideally, the ratio takes 1 in a frequency band to pass a signal component and 0 in a frequency band to cut off a signal component. The filter property in the illustrated example indicates a so-called low-pass filter type property in which 50% or more of a signal component passes in a band of 0 to fc [mHz] and 50% or more of a signal component is cut off in a band of fc [mHz] or more. fc=0.44 [mHz] will be called cutoff frequency below.

The horizontal axis in a broken line in the graph indicates frequency (unit: mHz) and the vertical axis indicates the amount of phase delay (unit: sec). Herein, the amount of phase delay is a difference of a phase of an output signal relative to a phase of an input cyclic signal (sinusoidal waveform signal), and ideally takes 0. The filter property in the illustrated example indicates a property in which a relatively large amount of phase delay is caused in a band of 0.1 to 0.9 [mHz] and a relatively small amount of phase delay is caused in a band of 0.9 [mHz] or more. An average value of the amount of phase delay in a band R1 at a cutoff frequency fc or less is on the order of 600 [sec].

Various well-known design methods for FIR filter or IIR (Infinite Impulse Response) filter may be applied for determining the first filter 48 (or a second filter 84 described below). For example, any of low-pass filter, high-pass filter, band-pass filter, band-rejection filter and all-pass filter may be applied for signal band pass. Any of Butterworth property, Chebyshev property, inverse Chebyshev property and alliance Chebyshev property (elliptic property) may be applied to a shape of the amplitude property.

[Relationship Between Filter Processing and Quantification Result]

Figure 5A:
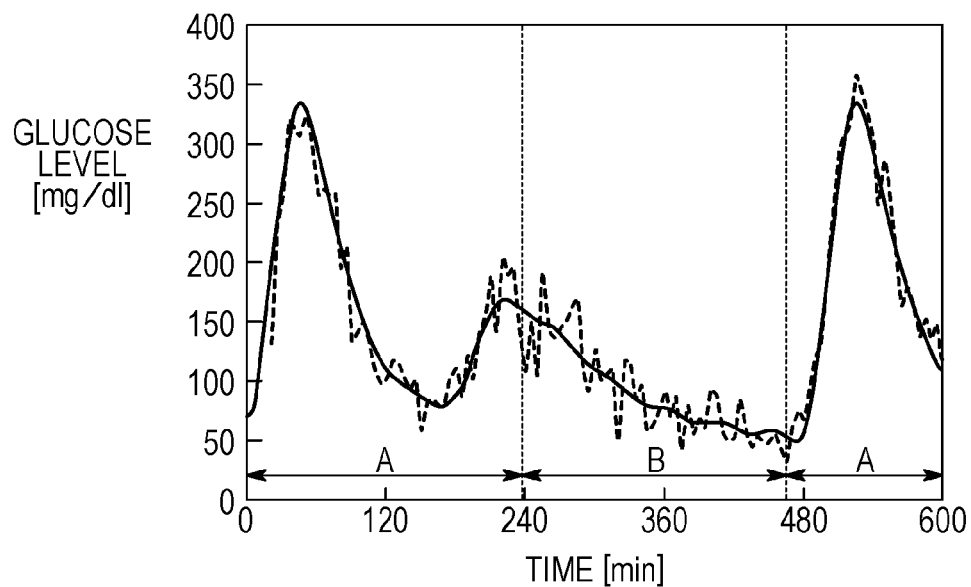
FIG. 5A is a graph indicating a change in concentration of glucose in blood and its quantification result.
Figure 5B:
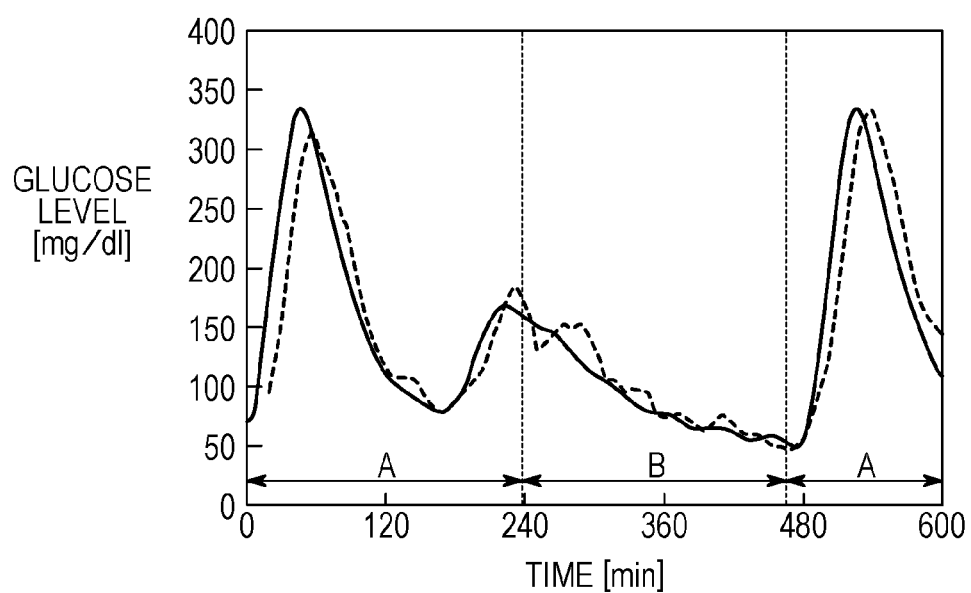
FIG. 5B is a graph indicating a change in concentration of glucose in blood and its quantification result.
Figure 6:
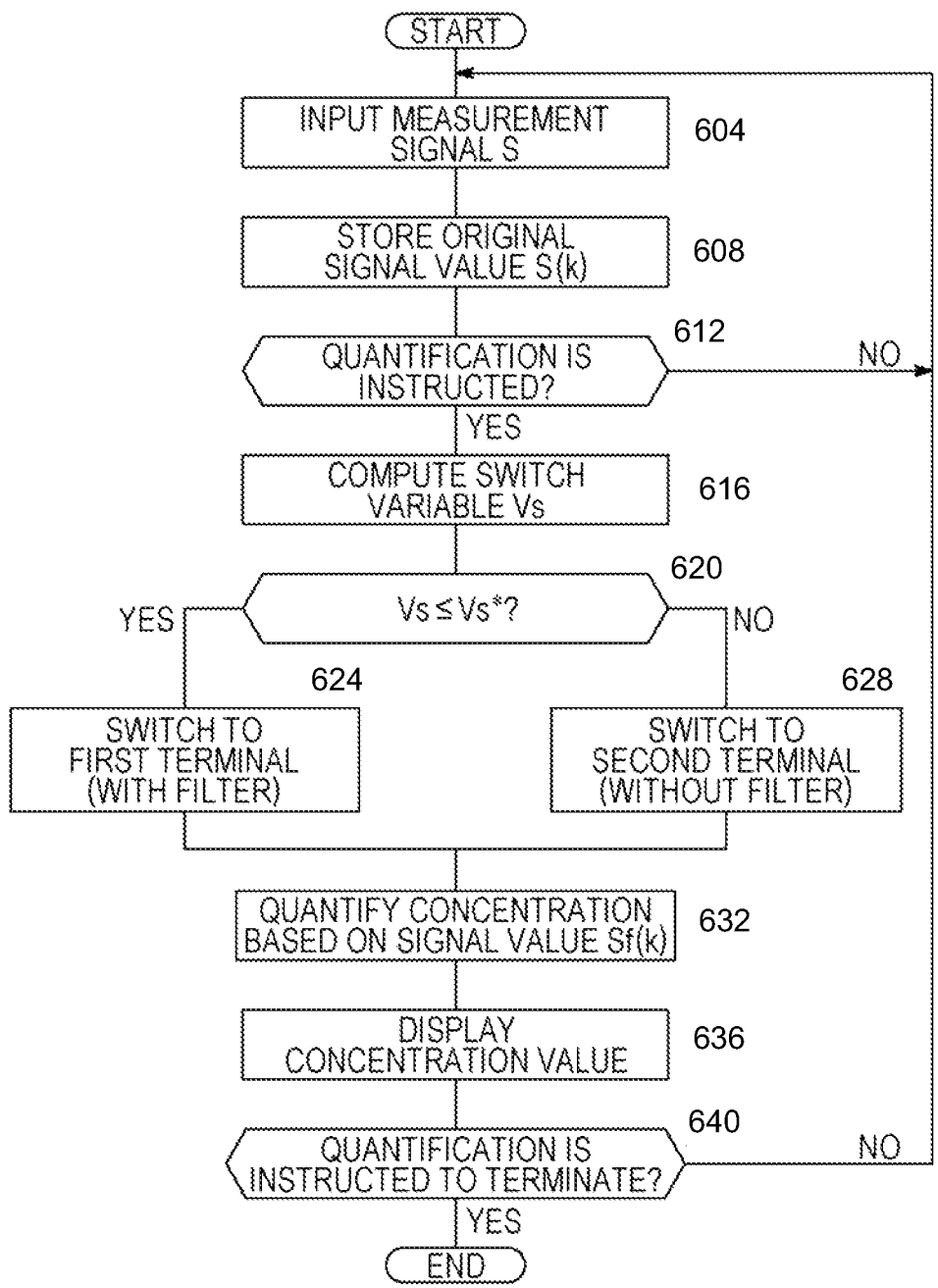
FIG. 6 is a flowchart for explaining the operations of the sensing device according to the first embodiment.

FIGS. 5A and 5B are the graphs indicating a change in concentration of glucose in blood and its quantification result. The horizontal axis in each graph indicates time (unit: min) and the vertical axis indicates glucose concentration or glucose level (unit: mg/dl). The changes in glucose level indicated in solid lines in the graphs simulate a temporal change in glucose level in the body before and after meal of a subject to be tested.

The graph in a broken line in FIG. 5A indicates a quantification result acquired without performing a filter processing on a measurement signal S. As understood from the graph, a high-frequency noise component is mixed into the measurement signal S, and thus irregular errors are caused between an actual value and a quantification value. In particular, an impact on quantification accuracy due to the noise component is conspicuously seen in the area B at a relatively low signal level.

The graph in a broken line in FIG. 5B indicates a quantification result acquired by performing a filter processing on the measurement signal S by the first filter 48. As understood from the graph, a quantification value with less irregular errors due to noise component is acquired. However, phase delay is caused by the first filter 48, and thus a gap is caused between an actual value and a quantification value. In particular, an impact on quantification accuracy due to a decrease in following capability is conspicuously seen in the area A with a large amount of temporal change in signal.

[Operations of Sensing Device 10 Including Sensor Control Circuit 14]

The presence of a filter is switched as needed with the sensing method according to the first embodiment in order to restrict the quantification errors from occurring. The operations of the sensing device 10 including the sensor control circuit 14 (see FIG. 2) will be described below in detail with reference to the flowchart of FIG. 6. The switch 44 in the filter processing unit 34 is assumed to be initially in the OFF state.

In step S1, the signal input unit 30 inputs a measurement signal S from the sensor unit 12 at a predetermined sampling interval Ts. Thereafter, the ADC 32 converts the analog signal acquired from the signal input unit 30 into a digital signal (denoted as original signal value S(k) below).

In step S2, the original signal value S(k) input and acquired in step S1 is temporarily stored in the buffer memory 40.

In step S3, the sensor control circuit 14 determines whether an instruction to quantify a concentration of analyte is made. Specifically, the sensor control circuit 14 determines whether a signal for instructing to quantify a concentration (denoted as quantification instruction signal below) is received from the calculation unit 16.

The calculation unit 16 counts the number of pulses of a clock signal input from the clock generator 24 while performing steps S1 and S2. Then, a count upper limit (corresponding to the quantification interval Td) is reached, the calculation unit 16 sends a quantification instruction signal to the sensor control circuit 14 and proceeds to next step (S4).

On the other hand, when the count upper limit is not reached, the calculation unit 16 continues to count the number of pulses without sending a quantification instruction signal. That is, the processing returns to step S1 to sequentially repeat steps S1 and S2.

The sampling interval Ts is a time interval at which a measurement signal S is input into the sensor control circuit 14 and the quantification interval Td is a time interval at which a concentration of analyte is quantified by the calculation unit 16. That is, the quantification interval Td is a different parameter from the sampling interval Ts, and thus may take the same or different value as or from the sampling interval Ts. When the quantification interval Td is equal to the sampling interval Ts, the sensor control circuit 14 may acquire and store an original signal value S(k) after receiving a quantification instruction signal.

In step S4, the switch variable computation unit 42 computes a switch variable Vs as a parameter indicating the amount of temporal change of a measurement signal S based on a time sequence of an original signal value S(k) sequentially stored in step S2. Herein, the amount of temporal change means a variation trend of the measurement signal S estimated based on a plurality of closest sample points.

Figure 7:
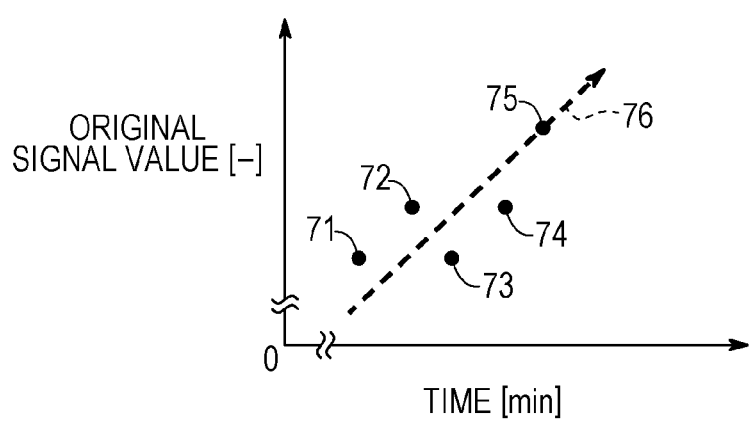
FIG. 7 is a schematic explanatory diagram illustrating how to compute the amount of temporal change based on a plurality of sample points by way of example.

As illustrated in FIG. 7, it is assumed that the sample points 74, 73, 72 and 71 are already acquired in temporally close order from a current sample point 75. In this case, not only the past sample points 71 to 74 but also the sample point 75 is used together thereby to find a regression line 76 indicated in a broken line. The switch variable computation unit 42 then computes the absolute value of a gradient (first derivation of time) of the regression line 76 as a switch variable Vs.

The method for computing a gradient may employ various optimization methods including weighted mean method and least square method. The number of sample points for trend estimation is not limited to five, and may be determined as needed in total consideration of the amount of calculations, a processing time, and the like. Further, the switch variable computation unit 42 may compute a switch variable Vs by use of, for example, statistic value (such as average value) of a line gradient connecting adjacent sample points or curvature (second derivation of time) in approximate curve, not limited to a gradient of the regression line 76.

In step S5, the filter processing unit 34 changes over the switch 44 in the filter processing unit 34 depending on a switch variable Vs computed in step S4. Specifically, the filter processing unit 34 determines a switch state of the switch 44 depending on a magnitude relationship with a present threshold Vs*.

When Vs≤Vs is met, the filter processing unit 34 changes over the switch 44 to the first terminal 46a for a certain period of time (step S6). Then, the original signal value S(k) is output to the outside of the sensor control circuit 14 via the switch 44, the first terminal 46a and the first filter 48.

When Vs>Vs is met, the filter processing unit 34 changes over the switch 44 to the second terminal 46b for a certain period of time (step S7). Then, the original signal value S(k) is output to the outside of the sensor control circuit 14 via the switch 44 and the second terminal 46b. In order to discriminate the terms below, an original signal value S(k) passing through the filtering unit 36 and output from the sensor control circuit 14 is referred to as "signal value Sf(k)."

The filter processing unit 34 may be provided with a dead band during a determination processing with the threshold Vs*. Thereby, fluctuations in a time-sequential determination result can be restricted, and filter processing control can be stably performed.

In step S8, the concentration quantification unit 29 quantifies a concentration based on a signal value Sf(k) output from the sensor control circuit 14 by use of a quantification coefficient or the like read from the RAM 22. Herein, the concentration quantification method may employ various methods suitable for detection system, material, sensitivity property, individual variability or the like in the sensor unit 12.

In step S9, the display 28 displays a quantification result in step S8. Prior to the display processing, the calculation unit 16 determines visible information (denoted as quantification visible information below) to be displayed on the display 28 among the acquired quantification results, and then supplies a control signal according to the quantification visible information to the display 28. The quantification visible information may include, for example, trend, whether to quantify or not, quantification time, diagnosis result, and the like, not only quantification value.

In step S10, the calculation unit 16 determines whether an instruction to terminate the series of quantification operations is made. When it is determined that an instruction to terminate is not made, the processing returns to step S1 to similarly repeat the operations in steps S1 to S9. On the other hand, when an instruction to terminate is made, the sensing device 10 terminates the analyte quantification operation. In this way, the calculation unit 16 acquires time-sequential data on a concentration at each point of time for quantification at a predetermined quantification interval Td.

[Operational Effects Obtained by Sensing Method According to First Embodiment]

The operational effects obtained by the sensing method according to the first embodiment will be described below with reference to FIG. 8. More specifically, the results quantified by use of different filter processings are compared based on the changes in concentration of glucose in blood illustrated in FIGS. 5A and 5B (in solid lines in the graphs). In both cases, the measurement and quantification are made assuming a sampling interval of Ts=5 [min] and a quantification interval of Td=5 [min]. Further, a threshold for the absolute value of a gradient of the regression line 76 (FIG. 7) is set at Vs*=0.3 [1/min].

Figure 8:
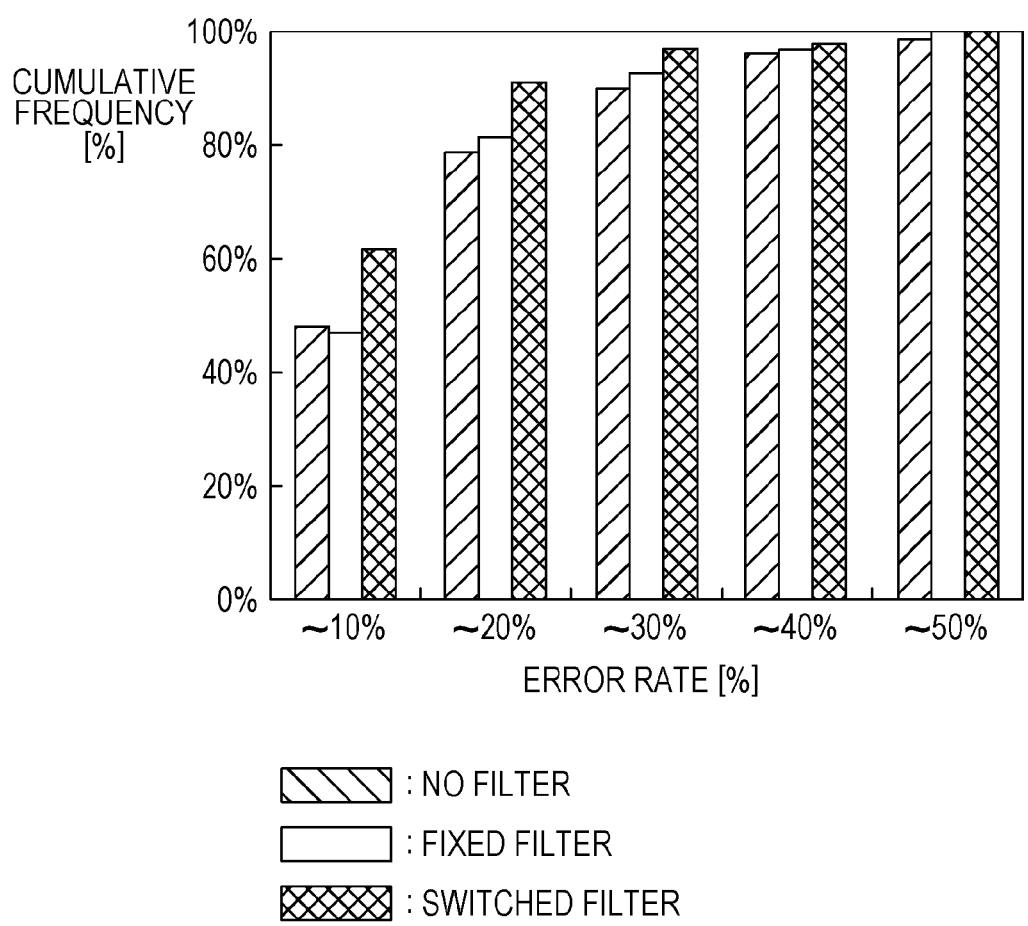
FIG. 8 is a cumulative histogram of quantification error rates of glucose during quantification with three types of filter processings.

FIG. 8 is a cumulative histogram of the glucose quantification error rates during quantification with three types of filter processings. The horizontal axis in the histogram indicates quantification value error rate (unit: %) and the vertical axis indicates cumulative frequency (unit: %).

"No filter" in the diagram corresponds to a quantification result when the switch 44 is always connected to the second terminal 46b (the graph in a broken line illustrated in FIG. 5A). "Fixed filter" corresponds to a quantification result when the switch 44 is always connected to the first terminal 46a (the graph in a broken line illustrated in FIG. 5B). "Switched filter" corresponds to a quantification result when the switch 44 is changed over as needed according to the flowchart of FIG. 6.

As understood from the drawing, a frequency at an error rate of 10% or less is higher in order of "switched filter">"no filter">"fixed filter." A frequency at an error rate of 20% or less is higher in order of "switched filter">"fixed filter">"no filter." In this way, it is concluded that the concentration quantification errors are significantly less with "switched filter" than with "no filter" and "fixed filter."

Second Embodiment

Subsequently, a structure and operations of the sensor control circuit 80 according to a second embodiment will be described with reference to FIGS. 9 to 12. The same constituents as those in the first embodiment are denoted with the same reference numerals, and an explanation thereof will be omitted.

[Block Diagram of Sensor Control Circuit 80]

Figure 9:
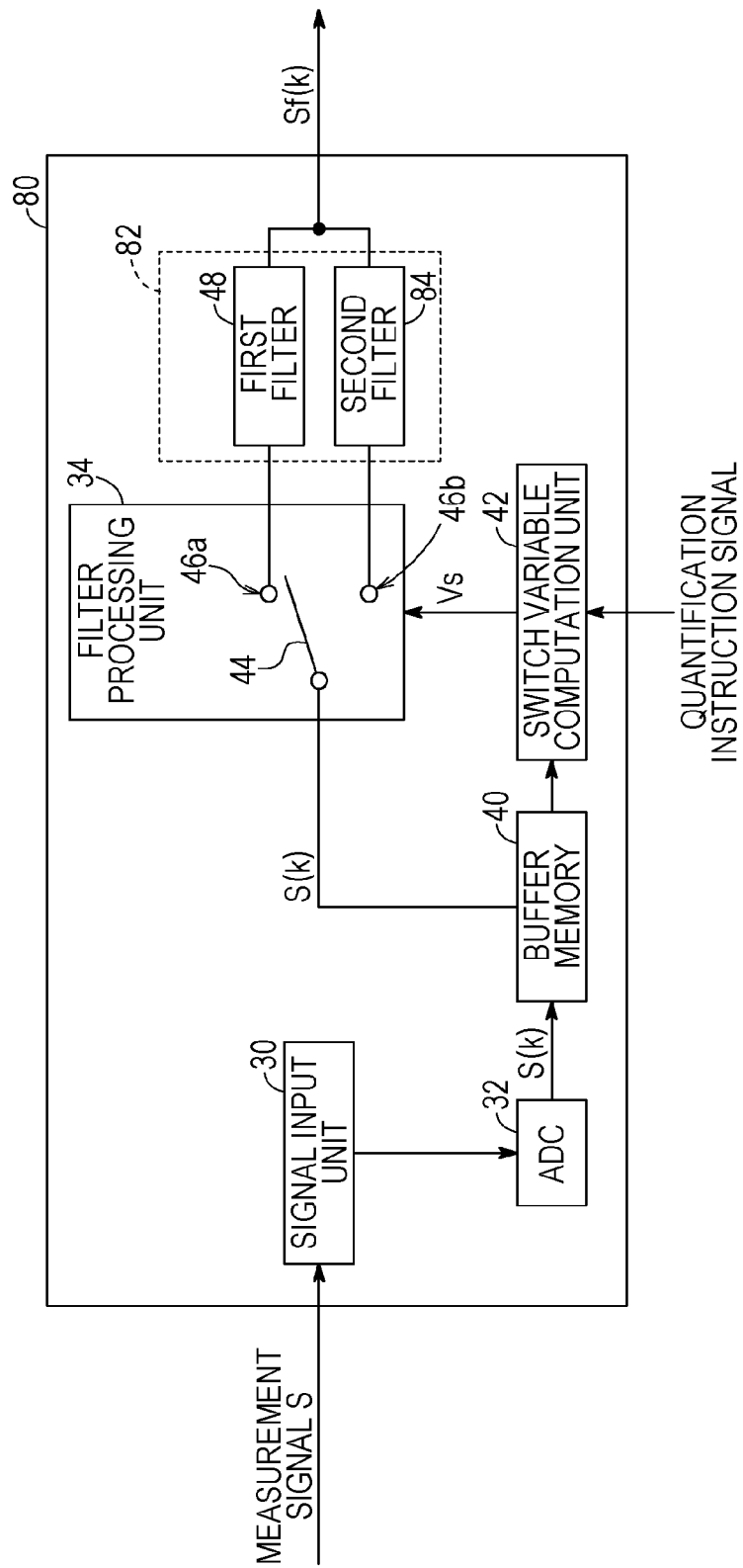
FIG. 9 is a block diagram of a sensor control circuit according to the second embodiment.

FIG. 9 is a block diagram of the sensor control circuit 80 (see FIG. 1) according to the second embodiment. The sensor control circuit 80 employs substantially the same structure as the sensor control circuit 14 (see FIG. 2), but includes a filtering unit 82 with a different structure instead of the filtering unit 36.

The filtering unit 82 includes the first filter 48, and the second filter 84 with the same circuit structure as the first filter 48 (see FIG. 3). The second filter 84 is connected to the second terminal 46b in the filter processing unit 34.

Figures 10A, 10B:
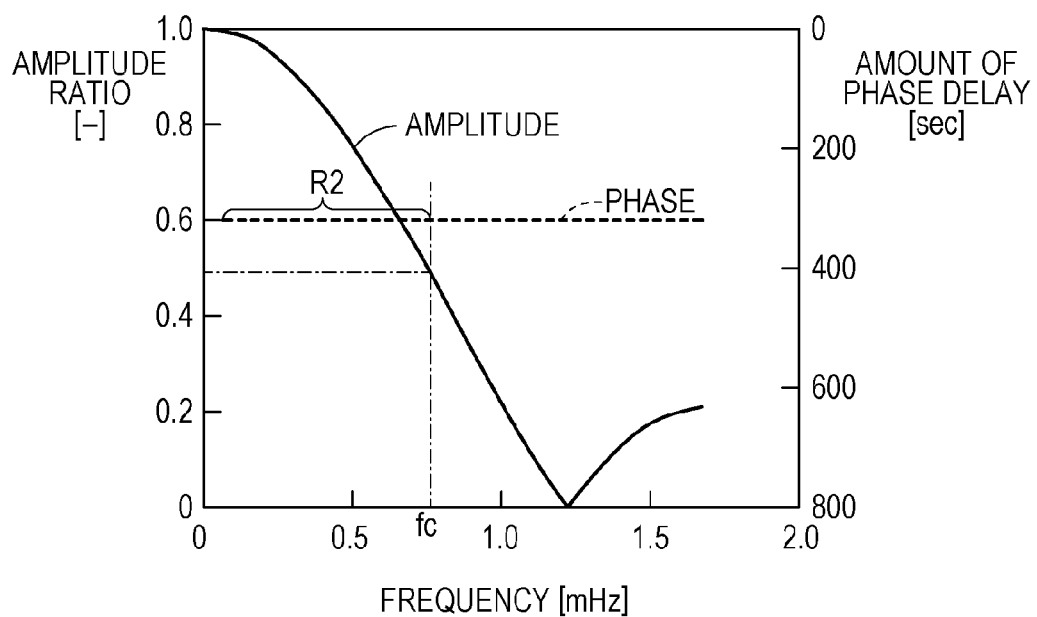
FIG. 10A is a diagram indicating filter coefficients of a second filter illustrated in FIG. 9.
FIG. 10B is a graph indicating a filter property depending on the filter coefficients of FIG. 10A.
Figure 11:
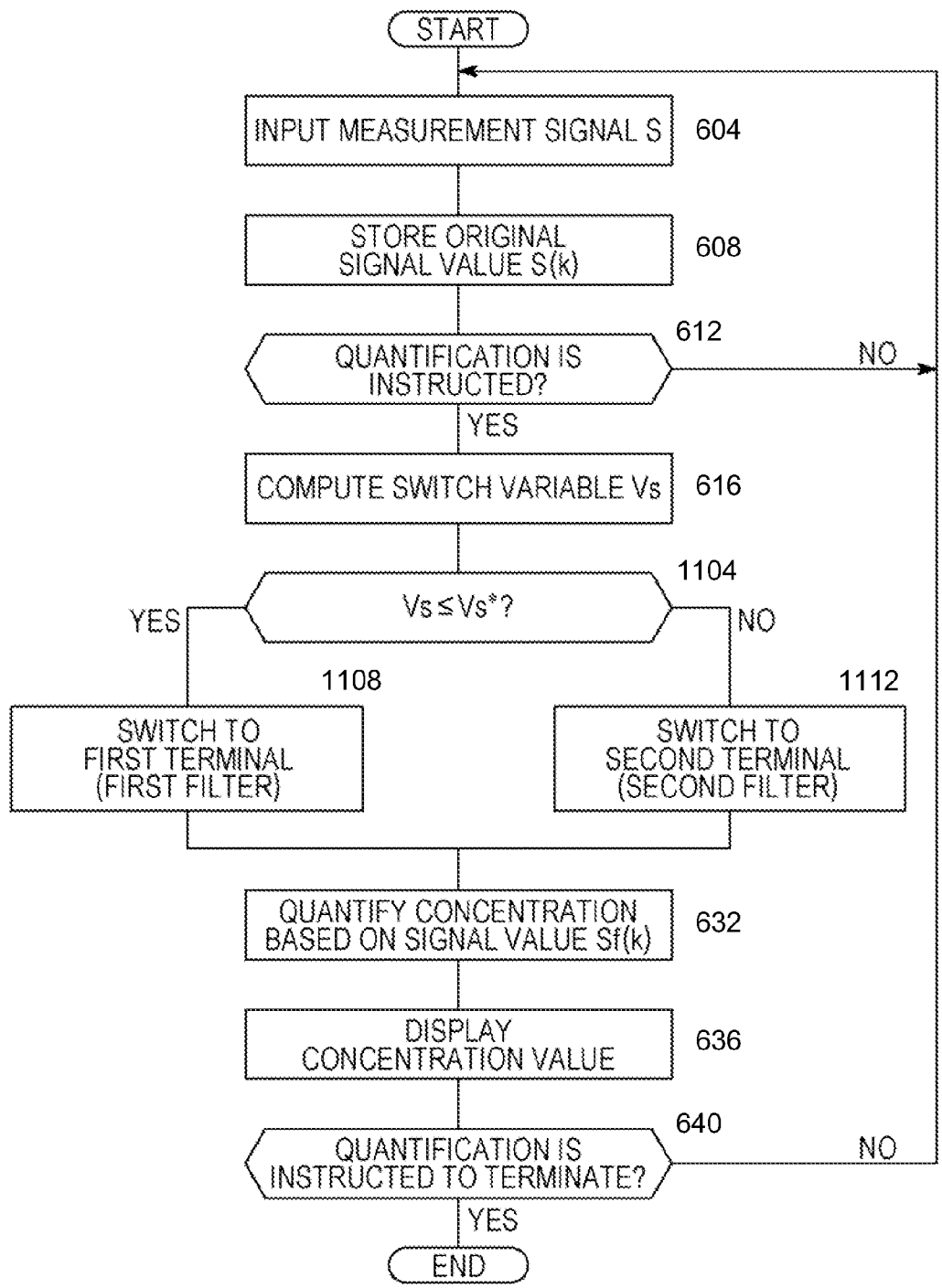
FIG. 11 is a flowchart for explaining the operations of the sensing device according to the second embodiment.

FIG. 10A is a diagram illustrating the filter coefficients of the second filter 84 illustrated in FIG. 9. Specifically, a filter coefficient of the multiplier 51 (see FIG. 3 below), a filter coefficient of the multiplier 52, a filter coefficient of the multiplier 53, a filter coefficient of the multiplier 54, and a filter coefficient of the multiplier 55 are set at h0=0.301, h1=0.398, h2=0.301, h3=0.000, and h4=0.000, respectively. In this way, the second filter 84 substantially functions as a FIR filter having three taps due to h3=h4=0.000.

FIG. 10B is a graph illustrating a filter property depending on the filter coefficients of FIG. 10A. The horizontal axis in a solid line in the graph indicates frequency (unit: mHz) and the vertical axis indicates amplitude ratio (unit: no). The filter property in the illustrated example indicates a low-pass filter type property similarly to FIG. 4B, where the cutoff frequency fc is at fc=0.74 [mHz]. That is, the cutoff frequency fc of the second filter 84 is higher than the cutoff frequency fc (=0.44) of the first filter 48.

The horizontal axis in a broken line in the graph indicates frequency (unit: mHz) and the vertical axis indicates the amount of phase delay (unit: sec). In the illustrated example, phase delay is substantially constant (=300 [sec]) in a band of 0 to 1.7 [mHz]. In this case, the average value of the amount of phase delay in the band R2 at a cutoff frequency fc or less is on the order of 300 [sec], which is lower than the average value (see FIG. 4B; about 600 [sec]) of the amount of phase delay in the first filter 48.

[Operations of Sensing Device 10 Including Sensor Control Circuit 80]

A plurality of types of filters is switched as needed in the sensing method according to the second embodiment in order to mutually complement the above disadvantages. The operations of the sensing device 10 including the sensor control circuit 80 (FIG. 9) will be described below with reference to the flowchart of FIG. 11. Steps S1 to S4 and steps S8 to S10 are the same as those in the flowchart of FIG. 6 (first embodiment), and thus an explanation thereof will be omitted.

In step S5, the filter processing unit 34 changes over the switch 44 depending on a computed switch variable Vs. When Vs≤Vs is met, the filter processing unit 34 changes over the switch 44 to the first terminal 46a for a certain period of time (step S6).

On the other hand, when Vs>Vs* is met, the filter processing unit 34 changes over the switch 44 to the second terminal 46b for a certain period of time (step S7A). Then, the original signal value S(k) is output to the outside of the sensor control circuit 80 via the switch 44, the second terminal 46b, and the second filter 84.

In this way, the calculation unit 16 acquires time-sequential data on a concentration at each point of time for quantification at a predetermined quantification interval Td.

[Quantification Result in Sensing Method According to Second Embodiment]

The operational effects obtained by the sensing method according to the second embodiment will be described below with reference to FIG. 12. More specifically, the results quantified by use of different filter processings are compared based on the changes (in solid lines in the graphs) in concentration of glucose in blood illustrated in FIGS. 5A and 5B. In both cases, the measurement and quantification are made assuming a sampling interval of Ts=5 [min] and a quantification interval of Td=5 [min]. Further, the threshold is set at Vs*=0.3 [1/min].

Figure 12:
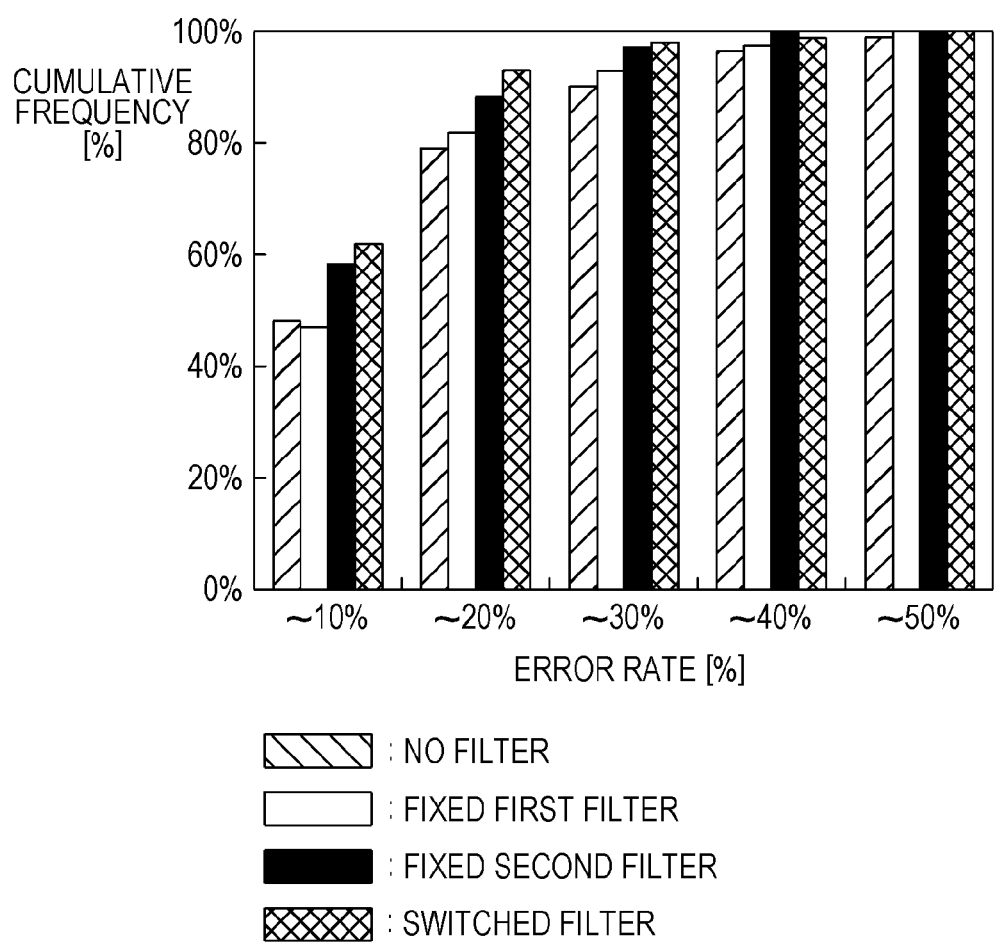
FIG. 12 is a cumulative histogram of quantification error rates of glucose during quantification with four types of filter processings.

FIG. 12 is a cumulative histogram of glucose quantification error rates during quantification with four types of filter processings. The horizontal axis in the histogram indicates quantification value error rate (unit: %) and the vertical axis indicates cumulative frequency (unit: %).

"No filter" and "fixed first filter" in the diagram correspond to "no filter" and "fixed filter" in FIG. 8, respectively. "Fixed second filter" corresponds to a quantification result when the switch 44 is always connected to the second terminal 46b. "Switched filter" corresponds to a quantification result when the switch 44 is changed over as needed according to the flowchart of FIG. 11.

As understood from the diagram, a frequency at an error rate of 10% or less is higher in order of "switched filter">"fixed second filter">"no filter">"fixed first filter." A frequency at an error rate of 20% or less is higher in order of "switched filter">"fixed second filter">"fixed first filter">"no filter." In this way, it is concluded that the concentration quantification errors are relatively less with "switched filter" than with "no filter", "fixed first filter" and "fixed second filter."

[Effects of the Present Invention]

As described above, the sensing device 10 includes the sensor unit 12 for sequentially acquiring a measurement signal S correlated with a concentration of analyte, and the filtering unit 36 or 82 for performing a filter processing on a time sequence of a measurement signal S in a frequency domain via one type of filter among a plurality of types of filters (48, 49, 84).

The filter processing unit 34 for switching one type of filter used in a filter processing in a frequency domain depending on the amount of temporal change of a measurement signal S (such as switch variable Vs) is provided, and thus the first filter 48 or the like can be selected as needed in total consideration of phase delay property due to a temporal change of the measurement signal and the filter processing. Thereby, a noise component can be effectively removed from a measurement signal S by use of a filter (such as the first filter 48) in a frequency domain with a relatively simple structure, while a following capability for a temporal change in concentration of analyte can be kept.

The filtering unit 36 includes at least the identity transformation filter 49 for performing identity transformation on a time sequence of a measurement signal S, and the filter processing unit 34 may switch to the identity transformation filter 49 when a switch variable Vs is higher than a threshold Vs*.

Further, the filtering unit 82 includes at least two types of filters (48, 84) with different average values of the amount of phase delay in a band at a cutoff frequency fc or less, and the filter processing unit 34 may switch to the second filter 84 with a low average value of the amount of phase delay when the switch variable Vs is high, and may switch to the first filter 48 with a high average value of the amount of phase delay when the switch variable Vs is low.

Phase delay is not caused by a filter processing when the switch variable Vs is high, and thus the following capability for a temporal change in concentration of analyte can be kept. Further, when the switch variable Vs is low, the following capability is less required, and thus a noise component can be more effectively removed from a measurement signal S.

The present invention is not limited to the embodiments, and may be freely modified without departing from the scope of the present invention.

For example, the filtering units 36 and 82 are configured in digital filter circuits in the first and second embodiments, but may be configured in analog filter circuits. When digital filters are applied, the filtering units may be realized in hardware and/or software. Further, when the filter processing is realized in software, it may be performed by the calculation unit 16 instead of the sensor control circuits 14 and 80.

What is claimed is:

1. A sensing device for continuously or intermittently quantifying a concentration of an analyte, comprising:
   a sensor sequentially acquiring a measurement signal correlated with the concentration of the analyte;
   a plurality of filters that perform filter processing on a time sequence of the measurement signal acquired by sensor in a frequency domain, the plurality of filters to eliminate noise components from the measurement signal, the plurality of filters at least comprising:
   a first filter;
   a second filter;
   a filter processing unit, wherein the filter processing unit receives a switch variable from a switch variable computation unit, the filter processing unit comprising:
   a switch, electrically coupled between the sensor and the plurality of filters;
   wherein the filter processing unit compares the switch variable to a predetermined threshold;
   wherein, if the switch variable is greater than the predetermined threshold, the filter processing unit signals the switch to route the measurement signal to the first filter;
   wherein, if the switch variable is less than the predetermined threshold, the filter processing unit signals the switch to route the measurement signal to the second filter.

2. The sensing device according to claim 1, wherein the first filter comprises an identity transformation filter for performing identity transformation on a time sequence of the measurement signal, and wherein the switch switches to the identity transformation filter when the switch variable is greater than the predetermined threshold.

3. The sensing device according to claim 1, wherein first filter has a low average value of an amount of phase delay in a band at a cutoff frequency or less, wherein the second filter has a high average value of an amount of phase delay in a band at a cutoff frequency or less; wherein the switch switches to the first filter when the switch variable is large; and wherein the switch switches to the second filter with a high average value of the amount of phase delay when the switch variable is small.

4. The sensing device according to claim 1, wherein the analyte is glucose.

5. The sensing device according to claim 1, wherein the first filter and/or second filter comprises one or more of a low-pass filter, a high-pass filter, a band-pass filter, a band-rejection filter, and an all-pass filter.

6. The sensing device according to claim 1, wherein the first filter and/or second filter comprises a finite impulse response (FIR) filter or an infinite impulse response (IIR) filter.

7. The sensing device according to claim 6, wherein the FR filter comprises five taps.

8. The sensing device according to claim 1, further comprising the switch variable computation unit to compute a switch variable that indicates an amount of temporal change of the measurement signal, wherein the switch variable is a variation trend of the measurement signal based on two or more measurement samples.

9. The sensing device according to claim 1, wherein the threshold is 0.3 [1/min].

10. The sensing device according to claim 1, wherein the first filter and/or second filter applies one of a Butterworth property, a Chebyshev property, an inverse Chebyshev property, and/or an alliance Chebyshev property to a shape of an amplitude property.

11. A sensing method for continuously or intermittently quantifying a concentration of an analyte, comprising:
    sequentially acquiring, by a sensor, a measurement signal correlated with the concentration of the analyte;
    determining a switch variable that indicates an amount of temporal change of the measurement signal;
    comparing the switch variable to a predetermined threshold;
    if the switch variable is greater than the predetermined threshold, switching, by a switch, the measurement signal to a first filter to perform filtering on a time sequence of the measurement signal acquired by the sensor in a frequency domain, wherein the first filter removes noise components from the measurement signal; and
    if the switch variable is less than the predetermined threshold, switching, by the switch; the measurement signal to a second filter to perform filtering on a time sequence of the measurement signal acquired by the sensor in a frequency domain, wherein the first filter removes noise components from the measurement signal, wherein the first and second filters are different.

12. The sensing method according to claim 11, wherein the first filter comprises an identity transformation filter for performing identity transformation on a time sequence of the measurement signal, and wherein the switch switches to the identity transformation filter when the switch variable is greater than the predetermined threshold.

13. The sensing method according to claim 12, wherein the first filter has a low average value of an amount of phase delay in a band at a cutoff frequency or less, wherein the second filter has a high average value of an amount of phase delay in a band at a cutoff frequency or less; wherein the switch switches to the first filter when the switch variable is large; and wherein the switch switches to the second filter with a high average value of the amount of phase delay when the switch variable is small.

14. The sensing method according to claim 11, wherein the first filter and/or second filter comprises one or more of a low-pass filter, a high-pass filter; a band-pass filter, a band-rejection filter, and an all-pass filter.

15. The sensing method according to claim 11, wherein the threshold is 0.3 [l/min].

16. The sensing method according to claim 11, wherein the analyte is glucose.

17. The sensing method according to claim 11, wherein any of the plurality of filters may apply one of a Butterworth property, a Chebyshev property, an inverse Chebyshev property, and an alliance Chebyshev property to a shape of an amplitude property.

18. A non-transitory computer readable medium having instructions for performing a method for continuously or intermittently quantifying a concentration of an analyte, the instructions comprising:
   instructions for sequentially acquiring, by a sensor, a measurement signal correlated with the concentration of the analyte;
   instructions for determining a switch variable that indicates an amount of temporal change of the measurement signal;
   instructions for comparing the switch variable to a predetermined threshold;
   if the switch variable is greater than the predetermined threshold, instructions for switching, by a switch, the measurement signal to a first filter to perform filtering on a time sequence of the measurement signal acquired by the sensor in a frequency domain, wherein the first filter removes noise components from the measurement signal; and
   if the switch variable is less than the predetermined threshold, instructions for switching, by the switch, the measurement signal to a second filter to perform filtering on a time sequence of the measurement signal acquired by the sensor in a frequency domain, wherein the first filter removes noise components from the measurement signal, wherein the first and second filters are different.

19. The computer readable medium according to claim 18, wherein the first filter and/or second filter comprises one or more of a low-pass filter, a high-pass filter, a band-pass filter, a band-rejection filter, an all-pass filter, a finite impulse response filter, an infinite impulse response filter, and/or an identity transformation filter.

20. The computer readable medium according to claim 19, further comprising instructions for computing the switch variable that indicates the amount of temporal change of the measurement signal, wherein the switch variable is a variation trend of the measurement signal based on two or more measurement samples.

* * * * *